United States Patent
Akerfeldt et al.

(12) 
(10) Patent No.: US 6,508,828 B1
(45) Date of Patent: Jan. 21, 2003

(54) SEALING DEVICE AND WOUND CLOSURE DEVICE

(75) Inventors: Dan Akerfeldt, Uppsala (SE); Per Egnelov, Uppsala (SE); Fredrik Preinitz, Uppsala (SE)

(73) Assignee: Radi Medical Systems AB, Uppsala (SE)

( * ) Notice: Subject to any disclaimer, the term of this patent is extended or adjusted under 35 U.S.C. 154(b) by 12 days.

(21) Appl. No.: 09/704,726

(22) Filed: Nov. 3, 2000

(51) Int. Cl.⁷ .............................................. A61B 17/04

(52) U.S. Cl. ...................................................... 606/215

(58) Field of Search ............................... 606/213, 215, 606/216, 217

(56) References Cited

U.S. PATENT DOCUMENTS

| | | | |
|---|---|---|---|
| 3,675,639 A | 7/1972 | Cimber | 128/1 |
| 3,874,388 A | 4/1975 | King et al. | 128/334 R |
| 4,007,743 A | 2/1977 | Blake | 128/334 R |
| 4,744,364 A | 5/1988 | Kensey | 128/334 |
| 4,852,568 A | 8/1989 | Kensey | 128/325 |
| 4,890,612 A | 1/1990 | Kensey | 606/213 |
| 4,917,089 A | 4/1990 | Sideris | 606/215 |
| 5,021,059 A | 6/1991 | Kensey et al. | 606/213 |
| 5,108,420 A | 4/1992 | Marks | 606/213 |
| 5,171,259 A | 12/1992 | Inoue | 606/213 |
| 5,192,302 A | 3/1993 | Kensey et al. | 606/213 |
| 5,342,393 A | 8/1994 | Stack | 606/213 |
| 5,350,399 A | 9/1994 | Erlebacher et al. | 606/213 |
| 5,531,759 A | 7/1996 | Kensey et al. | 606/213 |
| 5,620,461 A | 4/1997 | Van de Moer | 606/213 |
| 5,725,553 A * | 3/1998 | Moenning | 606/213 |
| 5,725,577 A | 3/1998 | Saxon | 623/11 |
| 5,861,004 A | 1/1999 | Kensey et al. | 606/213 |
| 6,328,743 B2 * | 12/2001 | Lerch | 606/215 |

FOREIGN PATENT DOCUMENTS

| | | |
|---|---|---|
| EP | 0 894 475 | 2/1999 |
| EP | 1 169 968 | 1/2002 |
| JP | 57-24132 | 5/1982 |
| SU | 1088709 | 4/1985 |
| WO | 90/14796 | 12/1990 |
| WO | 94/28800 | 12/1994 |
| WO | 99/40849 | 8/1999 |

OTHER PUBLICATIONS

Japanese Patent Application, Laid Open No. 2–307480, "Intravenous Atrial Septal Defect Hole Closing Device."

Umit T. Aker et al., "Immediate Arterial Hemostasis After Cardiac Catheterization.", Catheterization and Cardiovascular Diagnosis vol. 31, pp. 228–232, 1994.

Terry D. King et al., "Nonoperative closure of atrial septal defects.", Surgery, vol. 75, No. 3, pp. 383–388, 1974.

James E. Lock et al., "Transcatheter Closure of Patent Ductus Arteriosus in Piglets.", The American Journal of Cardiology, vol. 55, pp. 826–829, 1985.

James E. Lock et al., "Transcatheter Closure of Atrial Septal Defects.", Circulation, vol. 79, No. 5, pp. 1091–1099, 1989.

Noel L. Mills et al., "Umbrella catheter for nonoperative closure of atrial septal defects.", Medical Instrumentation, vol. 12, No. 1, pp. 65–69, 1978.

(List continued on next page.)

*Primary Examiner*—Ismael Izaguirre
(74) *Attorney, Agent, or Firm*—Foley & Lardner

(57) ABSTRACT

A sealing device and a wound closure device includes a sealing device for closing a wound in a wall of a vessel. The objective of the invention is to provide a sealing device and a wound closure device which has enhanced tightening properties. This problem is solved by the sealing device comprising an elongated member, which constitutes or is coated by a suture wire, having a constant thickness along its lock portion, the thickness being greater than the opening of the second sealing member. The sealing device is infinitely variable lockable along the distal lock portion.

14 Claims, 5 Drawing Sheets

OTHER PUBLICATIONS

William J. Rashkind et al., "Nonsurgical closure of patent ductus arteriosus: clinical application of the Rashkind PDA Occluder System.", Circulation, vol. 75, No. 3, pp. 583–592, 1987.

William J. Rashkind, "Transcatheter Treatment of Congenital Heart Disease.", Circulation, vol. 67, No. 4, pp. 711–716, 1983.

* cited by examiner

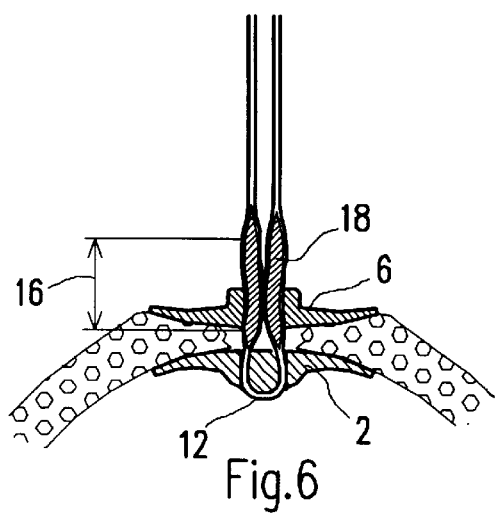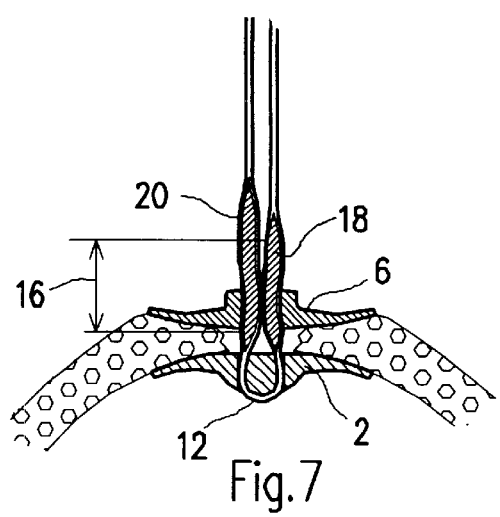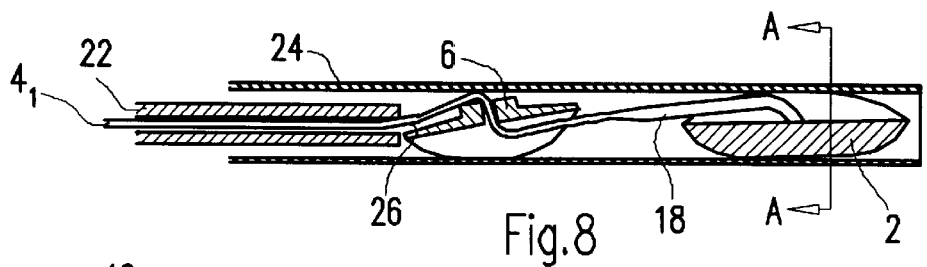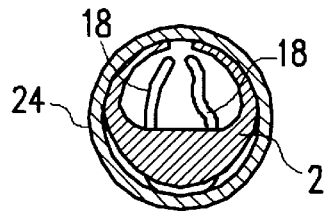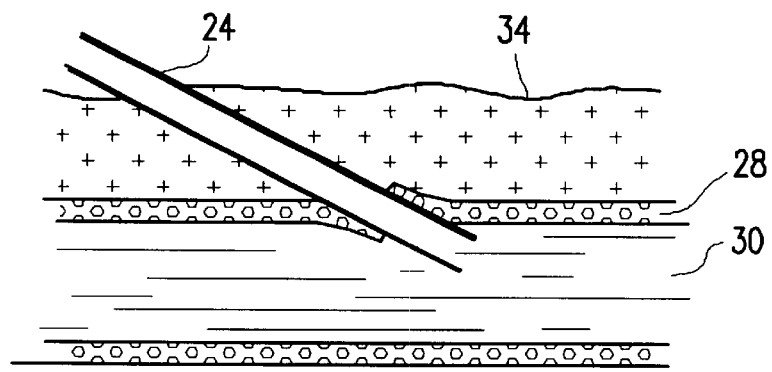

SEALING DEVICE AND WOUND CLOSURE DEVICE

FIELD OF THE INVENTION

The present invention relates to a sealing device and a wound closure device.

BACKGROUND

During certain types of medical surgery or treatment an introducer is used to access the vascular system of a patient. The introducer is inserted through the wall of a blood vessel in order to obtain access to the vascular system and may thereafter be used for guiding medical instruments such as catheters, guide wires and the like.

After the completion of the medical procedure there will be an incision or a wound in the wall of the blood vessel corresponding to the size of the introducer. The bleeding from the wound, which is the result of such a surgical operation, may be stopped by applying direct pressure on the wound. However, applying direct pressure on the wound will require assistance of medical personnel and may also restrict the blood flow through the vessel.

U.S. Pat. No. 5,342,393 describes a sealing device for sealing a perforation in the wall of a blood vessel. The device is in the form a two-part rivet, which seals the hole from both the inside and the outside of the vessel. Two rivet portions, an outer rivet portion and an inner rivet portion, are provided which are bayonet or screw threadedly interlocked to clamp the vessel wall. A problem with such a sealing device is that when screwing the outer rivet portion also the inner rivet portion will rotate since there is no holding-up on the inner rivet portion from the inside of the vessel, and thus it is hard to know if the sealing device is properly sealed or not. The latter may have disastrous consequences with blood leaking vessels.

U.S. Pat. No. 5,342,393 also discloses a sealing device, locked together via interlocking ridges. The inner rivet stem has triangular ridges that define horizontal shoulders and the outer rivet may have one or more upside down triangular ridges that define an opposing shoulder for engaging an adjacent shoulder and to thereby allow the outer rivet to be slid over the inner rivet but prevent separating movement. So in this sealing device, both the inner rivet stem and the outer rivet have so-called saw teeth.

The inventors have found that a problem with this sealing device is that the distance between the two occluders (i.e. rivets) may be varied only between fixed positions and thus cannot be exactly adapted to the thickness of the vessel. This in turn can lead to deteriorated tightening of the vessel if the distance exceeds the thickness of the vessel. On the other hand, it can also lead to the vessel being clamped with undue pressure on the vessel, which in turn might result in tissue necrosis or rupture of the arterial wall, when the distance is less than the thickness of the vessel.

U.S. Pat. No. 5,350,399 shows another sealing device for sealing a perforation in the wall of a blood vessel. The sealing device is constructed of a first member in the form of an intra-arterial occluder comprising a guide means in the form of an elongated wire integral with and extending centrally from the intra-arterial occluder and a second member in the form of an extra-arterial occluder. The guide includes a portion extending from the intra-arterial occluder which contains a plurality of saw teeth while the extra-arterial occluder is provided with an opening through which the guide passes. The saw teeth are wider in diameter than the opening in the extra-arterial occluder so that the extra-arterial occluder can be passed over the teeth in a direction towards the intra-arterial occluder.

The above mentioned problem, with the distance between the two occluders being varied only between fixed positions and thus cannot be exactly adapted to the thickness of the vessel, also arises in this sealing device.

A solution to the problem concerning saw teeth would be to provide very fine divided saw teeth, but this would be very unpractical and would give rise to manufacturing problems.

A sealing device commonly is inserted via an elongated introducer extending not perpendicular to the blood vessel, but in an acute angle towards the vessel, to get an insertion direction which is as close to the direction of the vessel as possible. This implies that the surfaces of the sealing device that are to be in contact with the surface of the vessel wall are not parallel to the surface of the vessel in the sealing moment, but in an acute angle to the surface of the vessel.

This reveals another problem in all the above mentioned sealing devices of prior art, if they have a rather stiff inner rivet stem portion extending centrally from the intra-arterial occluder. This problem concerns the difficulty of bringing the two occluders close enough to each other so as to tighten the vessel, because if the occluders cannot be adapted to the vessel wall, the vessel wall has to be deformed to fit towards the occluders which requires an increased sealing force between the occluders.

The angle also causes tensions to the elastic vessel wall since the vessel wall that is in contact with the sealing device becomes parallel to the surface of the occluders which makes the incision of the vessel wall dilated and the tightening more difficult.

The inventors found that these two problems do not arise at all when the sealing device surfaces are parallel to the vessel surface in the sealing moment, but the problem increases the larger the angle becomes.

The inventors found that if the inner rivet stem portion on the other hand is not stiff but flexible, the surface of the inner rivet portion will easy be adjusted to a position, which is parallel to the surface of the vessel. The stem closest to the inner rivet will be perpendicular to the inner rivet surface and the surface of the vessel, but be bent and making an arc, towards the acute angle of the elongated introducer where it thus is perpendicular to the surface of the outer rivet which is to be in contact with the surface of the vessel. The distance between the saw teeth on the stem will then be different on the outside and the inside of said arc, making it problematic to get a good engagement between the saw teeth on the stem and the outer rivet.

Thus there is a need in the art for a sealing device having improved and more secure sealing properties.

SUMMARY OF THE INVENTION

The objective problem to be solved by the present invention is to provide a sealing device for closing a wound, which has enhanced tightening properties.

This problem is solved by the invention described herein.

The invention is a device for closing a wound having an elongate member, a first sealing member, and a second sealing member. The second sealing member has an opening such that the second sealing member is threadable onto and along the elongate member. The elongate member includes a distal lock portion having a thickness greater than the opening of the second sealing member such that when the second sealing member is thread onto and along the elongate member, it is infinitely variable lockable along the distal lock portion.

Since the elongated member constitutes or is coated by a suture wire, and has a constant thickness along its lock portion, the thickness being greater than the opening of the second sealing member, the sealing device is infinitely variable lockable along the distal lock portion.

Preferred embodiments of the plug according to the invention are described below.

Thus, it is believed that the present invention provides a novel and easy-to-use sealing and wound closure device for closing a wound with excellent sealing properties.

BRIEF DESCRIPTION OF THE DRAWINGS

The foregoing and other aspects of the present invention will be best appreciated with reference to the following detailed description of specific embodiments of the invention, given by way of example only, when read in conjunction with the accompanying drawings, wherein:

FIG. 6 shows a sealing device for closing a wound in a wall of a vessel according to a second embodiment of the invention.

FIG. 7 shows a sealing device for closing a wound in a wall of a vessel according to a third embodiment of the invention.

FIG. 8 shows a wound closer device, which comprises the sealing device of any of the embodiments.

FIG. 9 shows a sectional view of a wound site, with an introducer extending through the vessel wall and into the vessel.

FIG. 18 shows a cross sectional view of the first sealing member compressed inside the introducer according to FIG. 8, seen along the line A—A.

DESCRIPTION OF THE PREFERRED EMBODIMENTS

Figure 1:
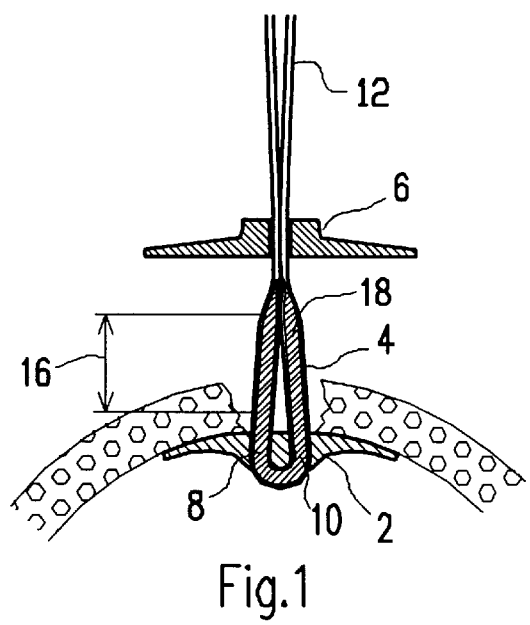
FIG. 1 shows a sealing device for closing a wound in a wall of a vessel according to a first embodiment of the invention.

FIG. 1 shows a sealing device for closing a wound in a wall of a vessel according to a first embodiment of the invention. The sealing device comprises three separate parts, namely a first sealing member 2, an elongated member 4 and a second sealing member 6. The first sealing member 2 is attached to a distal end of the elongate member 4. In this first embodiment of the sealing device, the first sealing member comprises two through openings 8, 10 (FIG. 2) through which a multifilament suture wire 12 is thread so as to make a pair of suture wires constituting the elongated member 4.

The second sealing member 6 is provided with an opening 14 (FIG. 3), which is adapted to the elongate member 4, i.e. the opening 14 is greater than the thickness of the proximal portion of the elongate member 4. With a structure like this the second sealing member 6 is threadable onto and along the elongate element 4 (FIG. 1). The most distal portion of the elongate member 4 has a constant thickness that is slightly greater than the opening 14 of the second sealing member 6 and constitutes the distal lock portion 16.

Figure 4:
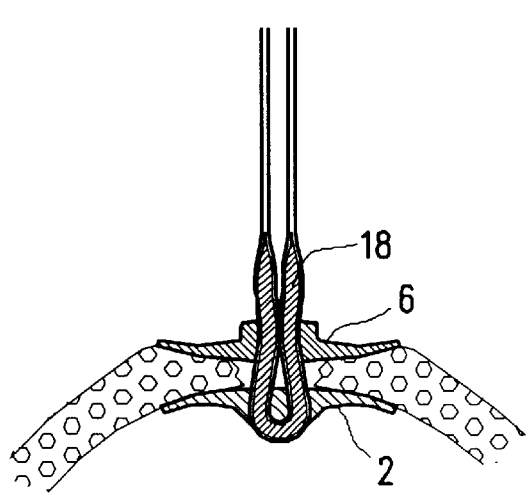
FIG. 4 shows a sealing device for closing a wound in a wall of a vessel according to a first embodiment of the invention.

This will allow for frictional engagement between inside of the opening 14 of the second sealing member 6 and the distal lock portion 16 of the elongate member 4 which makes the sealing device infinitely variable lockable along said distal lock portion 16 (FIG. 4).

The multifilament suture wire 12 is preferably made of a resorbable material such as Glycolic/Lactide polymer. The first sealing member 2 and second sealing member 6 are preferably made of a flexible resorbable material, such as Caprolactone/Trimethylene Carbonate/Glycolide polymer or any corresponding materials. Examples of suitable materials are described in an application entitled Amorphous Polymeric Polyaxial Initiators and Compliant Crystalline Copolymers Therefrom by S. W. Shalaby et al.

The choice of using a suture wire for the elongated element 4 is very important for the safe securing of the sealing device. Tests have been made to use the same material, e.g. a polymer, in the elongated member 4 as in the second sealing member 6. Since polymer gives a very glossy surface, it is hard to get high power frictional engagement between the elongated member 4 and the sealing member 6. Using a suture wire 12 for the elongate member 4 gives a safer sealing since the suture wire comprises a number of circulating fibres thus giving the wire a rough surface with a high frictional sealing power towards a glossy surface inside the opening 14 of the second sealing member 6.

The suture wire also makes the sealing device safer in another way. The suture wire is made in one piece and has very high tensile strength. It constitutes a continuous wire from the inner seal through the outer seal and to a tampering grip of the insertion tool, being threaded in through the first opening 8 and out again through the second opening 10 and thus keeping the sealing device safe together.

If a first sealing member and an elongated member are cast in one piece there is often problems with the casting process, giving the casted member air bubbles and inclusions and accordingly giving the sealing device poor structural strength.

The challenge is to make the suture wire 12 thicker in the distal lock portion 16.

In the first embodiment of the present invention, a hollow core of the suture wire 12 is filled with an elongated core 18

Figure 5:
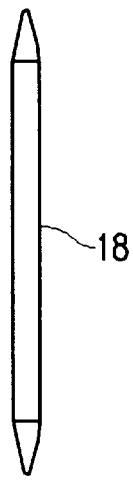
FIG. 5 shows an elongated core.

(FIG. 5), within the area of the distal lock portion 16 of the elongate member 4, but also in the area which is to be threaded through the first sealing member 2. (See again FIG. 1). The elongated core 18 is preferably made of a resorbable Caprolactone/Trimethylene carbonate/Glycolide polymer. This gives the suture wire 12 a thickening in the distal lock portion 16.

In a second embodiment of the present invention, shown in FIG. 6, the suture wire 12 is left unfilled within the area ranging from the entry of the first opening 8 of the first sealing member 2, through the first sealing member 2, out on the other side and in again through the second opening 10 of the first sealing member 2 to the exit of said second opening 10.

In a third embodiment of the present invention, shown in FIG. 7, the thickening of the first suture, of the two sutures making a pair of sutures, extends beyond the distal lock portion 16 into the proximal portion of the elongated member 4. This gives the suture wire 12 a more continuous increasing of the thickness which simplifies the threadening of the second sealing member 6 from the proximal portion onto the distal lock portion 16.

In a fourth embodiment of the present invention, instead of being filled, the suture 12 is thicker woven in the area of the distal lock portion.

Figure 15:
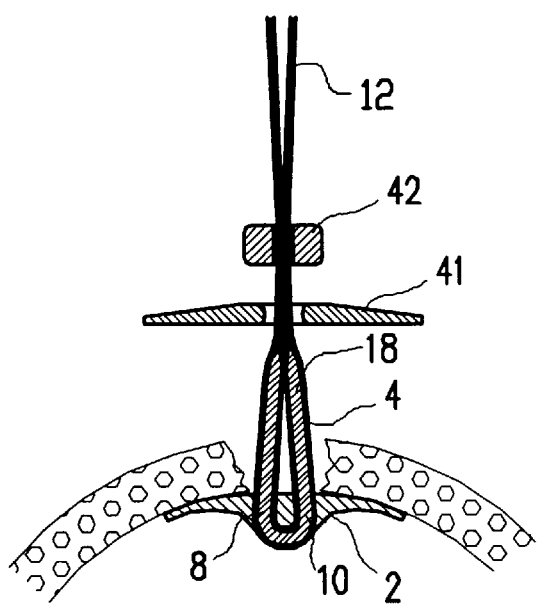
FIG. 15 shows a sealing device for closing a wound in a wall of a vessel according to a fifth embodiment of the invention.
Figure 16:
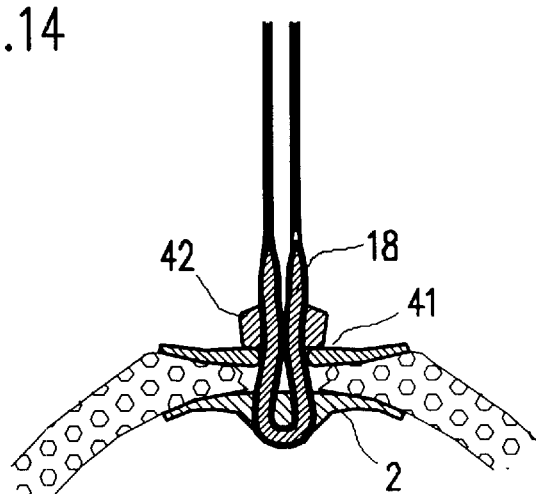
FIG. 16 shows a sealing device for closing a wound in a wall of a vessel according to a fifth embodiment of the invention.

In a fifth embodiment of the present invention, (FIGS. 15 and 16) the second sealing member is divided into two parts, which first part 41 is a plate and is provided with an opening that is approximately the same or slightly greater than the thickness of the distal lock portion 16. This first part 41 is threadable onto and along the elongate member 4 (FIG. 15), over the distal lock portion until it is in contact with the outside of the vessel wall. The first part plate 41 is preferably quite thin, which makes it flexible and easy to adapt to the vessel wall. The second part 42 is provided with an opening that is slightly smaller than the thickness of the distal lock portion 16. This second part 42 is threadable onto and along the elongate member 4 (FIG. 15), over the distal lock portion until it is in contact with the first part 41. The second part 42 allows for frictional engagement between the inside of the opening of the second part 42 and the distal portion 16 (FIG. 16). The second part 42 is preferably thicker than the first part 41, which gives it a large surface inside its opening for said frictional engagement. On the other hand, the diameter of the second part 42 is preferably smaller than the first part 41.

Figure 17:
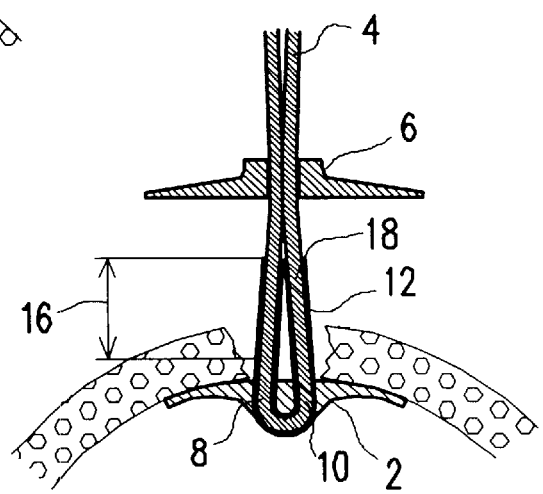
FIG. 17 shows a sealing device for closing a wound in a wall of a vessel according to a sixth embodiment of the invention.

In a sixth embodiment, the elongated portion 4 is not a suture wire, but another material, e.g. a resorbable polymer (FIG. 17). The distal lock portion 16 is coated by a hollow suture wire like a stocking so that a decent frictional engagement can be achieved between said coated distal lock portion and the inside of the opening of the second sealing member.

Typical dimensions of parts of the sealing device are for the first and second openings 8 and 10 of the first sealing member 2, a diameter of 0.2 mm, and for the opening 14 of the second sealing member 6, a diameter of 0.5 mm. The typical dimension of the suture is a diameter of 0.25 mm and of the distal lock portion 16, a diameter of 0.4 mm and a length of 8 mm.

Figure 2:
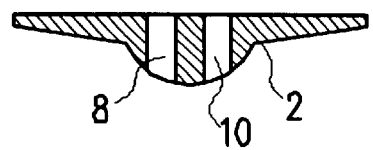
FIG. 2 shows a sectional view of a first sealing member.
Figure 3:
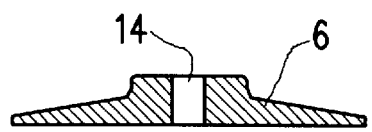
FIG. 3 shows a sectional view of a second sealing member.

FIG. 2 and FIG. 3 show respectively a sectional view of an example of a first sealing member 2 and a second sealing member 6 according to the embodiments of the invention. The first and second sealing member 2, 6 will pass through an introducer 24 (see FIG. 8) on the way to its final position in the wound. Since the first and second sealing member 2, 6, each has a diameter that is greater than the diameter of the introducer 24, they are made compressible. The first and second sealing member 2 and 6, according to the present invention, are preferably built up of portions that are foldable and portions that are more rigid, but other shapes are also possible. FIG. 18 shows a cross sectional view of the first sealing member 2 compressed inside the introducer 24 according to FIG. 8, seen along the line A—A.

FIG. 8 shows a wound closer device, which comprises the sealing device of any of the embodiments, mentioned above and a pusher 22 adapted for pushing the first sealing member 2, the elongated member 4 and the second sealing member 6 through an introducer 24.

The sealing device will be passed through the introducer 24 in order to reach its final position in the wound to be closed. To achieve this, the pusher 22 may be used to push the first sealing member 2, the elongated member 4 and the second sealing member 6 through the introducer 24. The pusher 22 has a size adapted to the size of the introducer 24, i.e. the diameter of pusher 22 is smaller than the inner diameter of the introducer 24 such that the elements of the sealing device can be pushed through the introducer 24. Furthermore, the pusher 22 is provided with a through hole 26 along the longitudinal axis thereof. This through hole 26 is large enough to accommodate the elongate member 4.

It will now be described how the different elements of the wound closure device operate and their relation to each other.

FIG. 9 shows a sectional view of a wound site, with an introducer 24 extending through the vessel wall 28 and into the vessel 30. The introducer 24 is introduced through the skin and passes the tissue 34 before it penetrates the vessel wall 28 and enters the vessel 30. When the introducer 24 is removed a wound will be left in the vessel wall 28. It is that wound that the wound closer device according to the present invention will close, with use of the wound closure device and sealing device described above.

Figure 10:
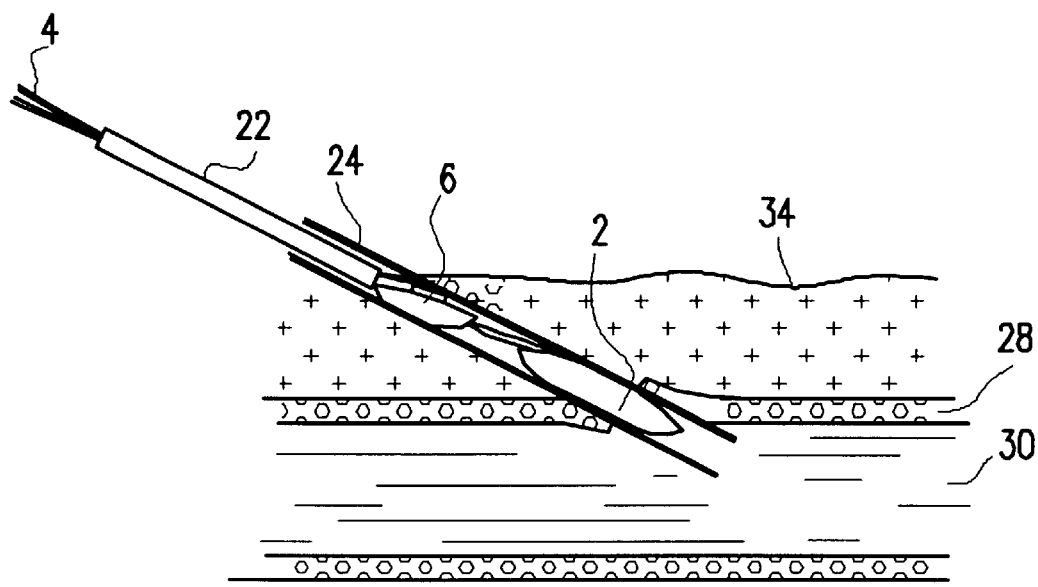
FIG. 10 shows a sectional view of the wound site, with the pusher, the first sealing member, the elongated member and the second sealing member, inside of the introducer.
Figure 11:
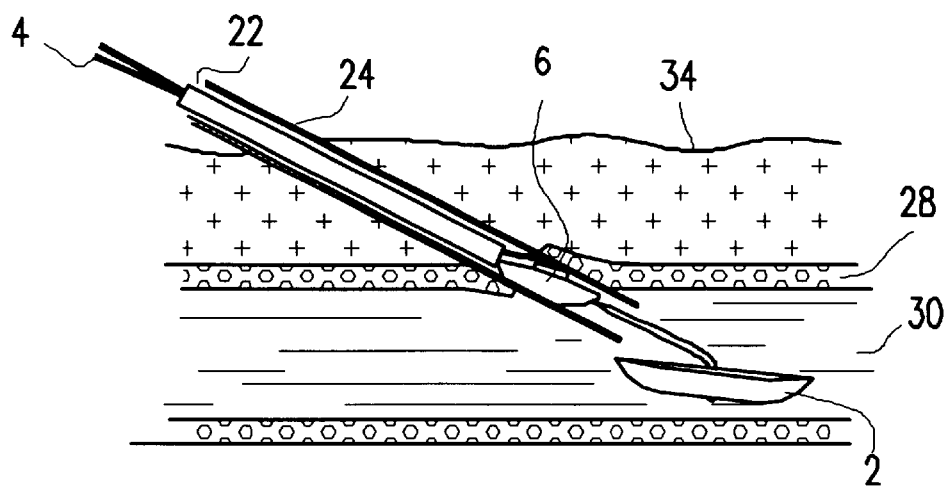
FIG. 11 shows a sectional view of the wound site wherein the first sealing member extends outside of the introducer and into the vessel.

FIG. 10 shows a sectional view of the wound site, with the pusher 22, the first sealing member 2, the elongated member 4 and the second sealing member 6, inside of the introducer 24. As can be seen in FIG. 10, the first sealing member 2 has been pushed such that it is situated in the distal end of the introducer 24. The first sealing member 2 is in a compressed state. Thereafter, the pusher 22 is pushed until a first sealing (not shown) of the pusher 22 abuts the proximal end of the introducer 24 and the first sealing member 2 has reached the state shown in FIG. 11. In this state the first sealing member 2 extends outside of the introducer 24 and into the vessel 30. As soon as the first sealing member 2 is outside of the introducer 24 it will unfold to an expanded state.

Figure 12:
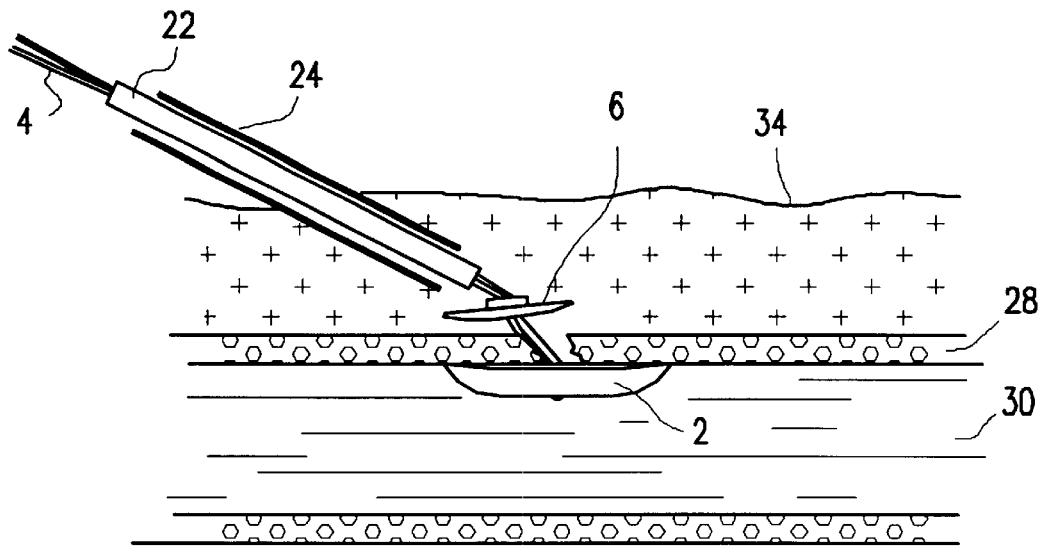
FIG. 12 shows a sectional view of the wound site wherein the introducer is drawn out of the vessel 30 and the second sealing member is pushed outside the introducer.

FIG. 12 shows the next state, wherein the introducer 24 is drawn out of the vessel 30 until it reaches the tissue outside of the vessel wall 28. The second sealing member 6 is pushed outside the introducer 24.

Figure 13:
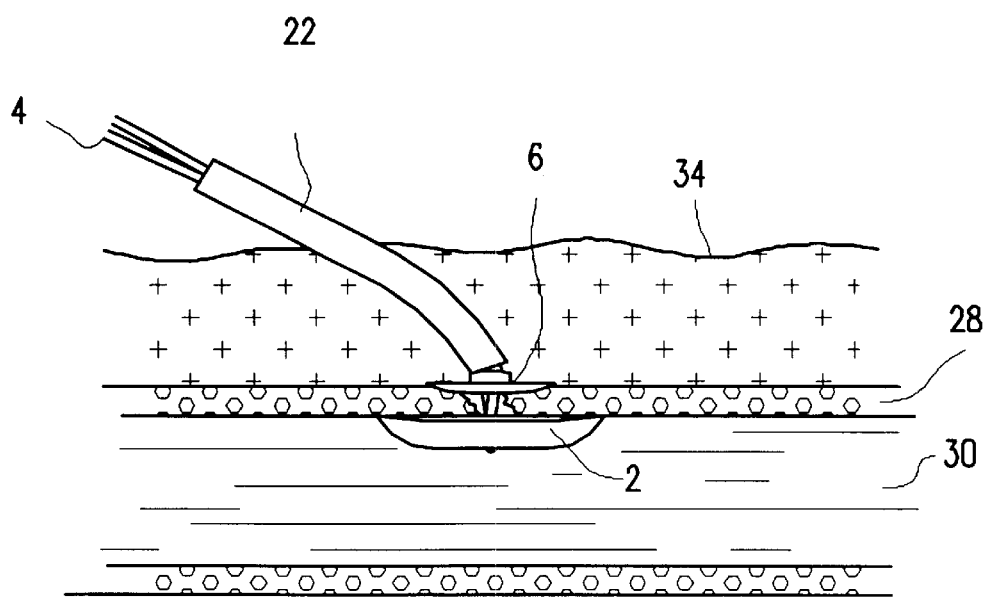
FIG. 13 shows a sectional view of the wound site wherein the second sealing member is pushed into its final position.

Thereafter the pusher 22 pushes the second sealing member 6 along the elongated member 4, over the distal lock portion 16, into its final position. (FIG. 13.) During the process of bringing the second sealing member 6, the elongate member 4 of the first sealing member 2 will act as a guide towards that position. The second sealing member 6 is threadable onto and along the elongate member 4. When the second sealing member 6 is close to its final position, the elongate member 4 onto which it is threaded increases in diameter. The second sealing member 6 will therefore be in frictional engagement with the elongated member 4 when it reaches its final position.

Figure 14:
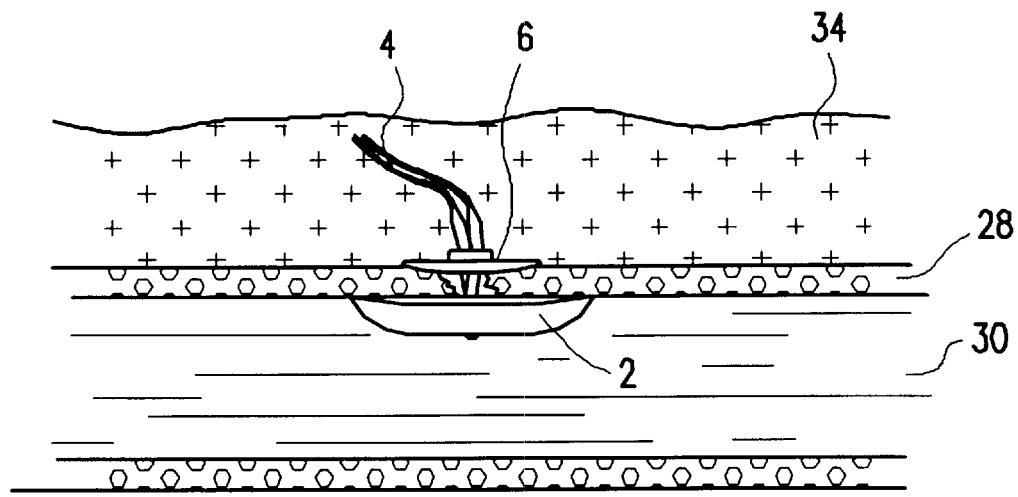
FIG. 14 shows a sectional view of the wound site wherein the sealing device closes the wound and the pusher and the introducer are removed.

Thereafter the pusher 22 and the introducer 24 are removed and the sealing device closes the wound as can be seen in FIG. 14.

Since the second sealing member 6 is threadable onto and along the elongated member 4, it is possible to adapt the sealing device to wounds having different thickness. One of the great advantages with the sealing device of the present invention is that it is adaptable to the thickness of the wound or vessel wall 28.

It shall be noted that the different features depicted in the figures are not drawn in scale. The purpose of the figures is not to limit the invention to the dimensions or relations shown, but instead make it easy to understand the principles of the present invention.

Whilst this invention has been described in terms of preferred embodiments thereof, it will be appreciated that other forms could readily be adapted by one skilled in the art. The invention can be applied to wounds other than in blood vessels. Additional information is disclosed in provisional patent application No. 60/204118, filed May 15, 2000, whose entire contents are incorporated herein by reference.

Accordingly, the scope of this invention is to be considered limited only by the following claims and equivalents thereof.

What is claimed is:

1. A device for closing a wound, said device comprising:
   an elongate member;
   a first sealing member; and
   a second sealing member, said second sealing member having an opening such that said second sealing member is threadable onto and along the elongate member;
   wherein said elongate member includes a distal lock portion having a thickness greater than said opening of the second sealing member such that when said second sealing member is thread onto and along the elongate member, it is infinitely variable lockable along said distal lock portion.

2. A device for closing a wound in a wall of a vessel, said device comprising:
   a first sealing member attached to a distal end of an elongate member; and
   a second sealing member, said second sealing member having an opening such that said second sealing member is threadable onto and along the elongate member;
   said elongate member including a proximal portion with a thickness smaller than said opening and a distal lock portion;
   wherein said elongate member is a suture wire and said distal lock portion has a constant thickness along said lock portion, said thickness being greater than said opening of the second sealing member, so that when said second sealing member is thread onto and along the elongate member, it is infinitely variable lockable along said distal lock portion.

3. A device according to claim 2, wherein said suture comprises a hollow core, which hollow core includes material to thicken the suture in the distal lock portion.

4. A device according to claim 3, wherein the thickness of the distal lock portion of the elongate member is adapted for frictional engagement to the second sealing member.

5. A device according to claim 2, wherein the elongate member is a pair of suture wires.

6. A device according to claim 3, wherein the elongate member is a pair of suture wires.

7. A device according to claim 2, wherein the second sealing member is divided into two parts, a first part and a second part, which first part is a plate and is provided with an opening that is the same or greater than the thickness of the distal lock portion, and the second part is provided with an opening that is smaller than the thickness of the distal lock portion and which second part allows for frictional engagement between the inside of an opening of the second part and the distal lock portion.

8. A device according to claim 2, further comprising:
   a pusher adapted for pushing, through an introducer, the first sealing member and the elongate member through a wound in a vessel wall and the second sealing member towards the outside of said wound to frictional engagement to the elongate member.

9. A device for closing a wound in a wall of a vessel, said device comprising:
   a first sealing member attached to a distal end of an elongate member; and
   a second sealing member, said second sealing member having an opening such that said second sealing member is threadable onto and along the elongate member;
   said elongate member including a proximal portion with a thickness smaller than said opening and a distal lock portion;
   wherein said distal lock portion is coated by a hollow stocking-like suture wire such that said distal lock portion has a constant thickness along the lock portion, said thickness being greater than said opening of the second sealing member, such that when said second sealing member is thread onto and along the elongate member it is infinitely variable lockable along said distal lock portion.

10. A device according to claim 9, further comprising:
    a pusher adapted for pushing, through an introducer, the first sealing member and the elongate member through a wound in a vessel wall and the second sealing member towards the outside of said wound to frictional engagement to the elongate member.

11. A device according to claim 1, wherein the thickness of the distal lock portion of the elongate member is adapted for frictional engagement to the second sealing member.

12. A device according to claim 2, wherein the thickness of the distal lock portion of the elongate member is adapted for frictional engagement to the second sealing member.

13. A device according to claim 1, wherein the second sealing member is divided into two parts, a first part and a second part, which first part is a plate and is provided with an opening that is the same or greater than the thickness of the distal lock portion, and the second part is provided with an opening that is smaller than the thickness of the distal lock portion and which second part allows for frictional engagement between the inside of an opening of the second part and the distal lock portion.

14. A device according to claim 1, further comprising:
    a pusher adapted for pushing, through an introducer, the first sealing member and the elongate member through a wound in a vessel wall and the second sealing member towards the outside of said wound to frictional engagement to the elongate member.

* * * * *